Figure 1:
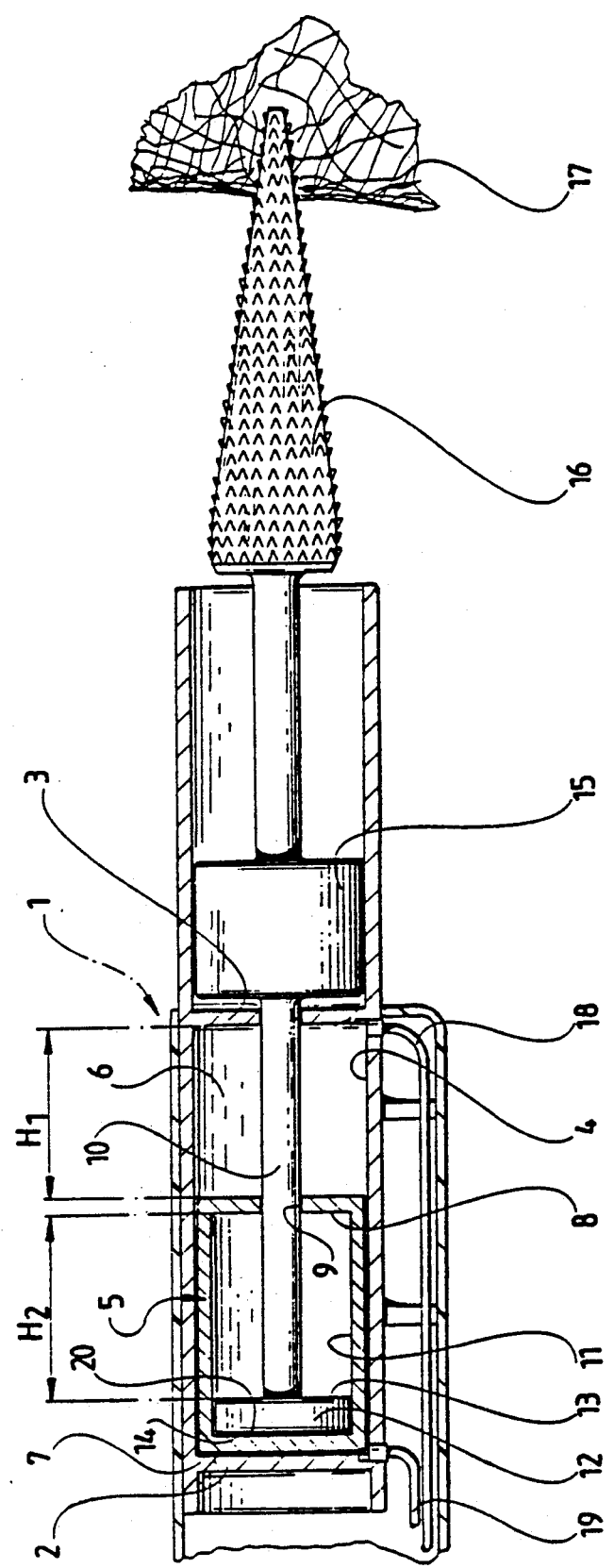

ically driven piston which is
United States Patent [19]
Appel et al.

[11] Patent Number: 5,108,400
[45] Date of Patent: Apr. 28, 1992

[54] STRIKING TOOL FOR SURGICAL INSTRUMENTS

[75] Inventors: Hans-Günter Appel, Accum; W. A. Laabs, Wilhelmshaven; Thorsten Heymeyer, Schiffdorf-Wehdel; Rainer Häusler, Tuttlingen; Wilfried Wölfle, Dürrheim, all of Fed. Rep. of Germany

[73] Assignee: Aesculap AG, Fed. Rep. of Germany

[21] Appl. No.: 401,451

[22] PCT Filed: Jan. 19, 1989

[86] PCT No.: PCT/EP89/00059
§ 371 Date: Sep. 14, 1989
§ 102(e) Date: Sep. 14, 1989

[87] PCT Pub. No.: WO89/06516
PCT Pub. Date: Jul. 27, 1989

[30] Foreign Application Priority Data
Jan. 21, 1988 [DE] Fed. Rep. of Germany ....... 3801676
Jan. 25, 1988 [DE] Fed. Rep. of Germany ....... 3802033

[51] Int. Cl.⁵ .......................... A61F 5/04; B25D 9/00
[52] U.S. Cl. .......................... 606/79; 606/80; 173/91
[58] Field of Search .......... 606/79, 80, 81, 84, 606/85, 100, 101, 99; 173/91, 131, 132, 134

[56] References Cited
U.S. PATENT DOCUMENTS

| | | | |
|---|---|---|---|
| 1,014,295 | 1/1912 | Gibb | 173/91 |
| 2,655,921 | 10/1953 | Haboush | 606/84 |
| 3,456,739 | 7/1969 | Sagae | 173/91 |
| 3,583,499 | 6/1971 | Cordes | 173/91 |
| 3,891,036 | 6/1975 | Schmidt | 173/91 |
| 4,114,950 | 9/1978 | Cooper | 173/91 |
| 4,121,672 | 10/1978 | Tkach | 173/91 |
| 4,706,659 | 11/1987 | Matthews | 606/80 |
| 4,840,237 | 6/1989 | Roemer | 173/91 |
| 4,886,128 | 12/1989 | Roemer | 173/91 |

FOREIGN PATENT DOCUMENTS
0144005 6/1985 European Pat. Off. ............. 606/79
3229309 5/1987 Fed. Rep. of Germany .

Primary Examiner—Robert A. Hafer
Assistant Examiner—Michael Brown
Attorney, Agent, or Firm—Barry R. Lipsitz

[57] ABSTRACT

In a striking tool for surgical instruments with a sleeve-shaped gripping part, a tool holder which is slidingly displaceable in the latter in the longitudinal direction thereof, and an oscillatingly driven piston which is slidingly displaceable in the gripping part in the longitudinal direction thereof and has two striking surfaces which strike corresponding contact surfaces of the tool holder and thereby act upon the latter with impulses acting in opposite directions, to enable selective generation of blows in the striking direction and in the pulling-out direction without converting the tool, it is proposed that the actual stroke of the piston in the gripping part be limited such that is it smaller than the double-strike stroke which the piston would have to cover, with the tool holder held firmly in the gripping part, from the striking of the first striking surface against the contact surface to the striking of the second striking surface against the second contact surface, and that the tool holder be mounted for sliding displacement in the gripping part both relative to the gripping part and relative to the piston.

12 Claims, 3 Drawing Sheets

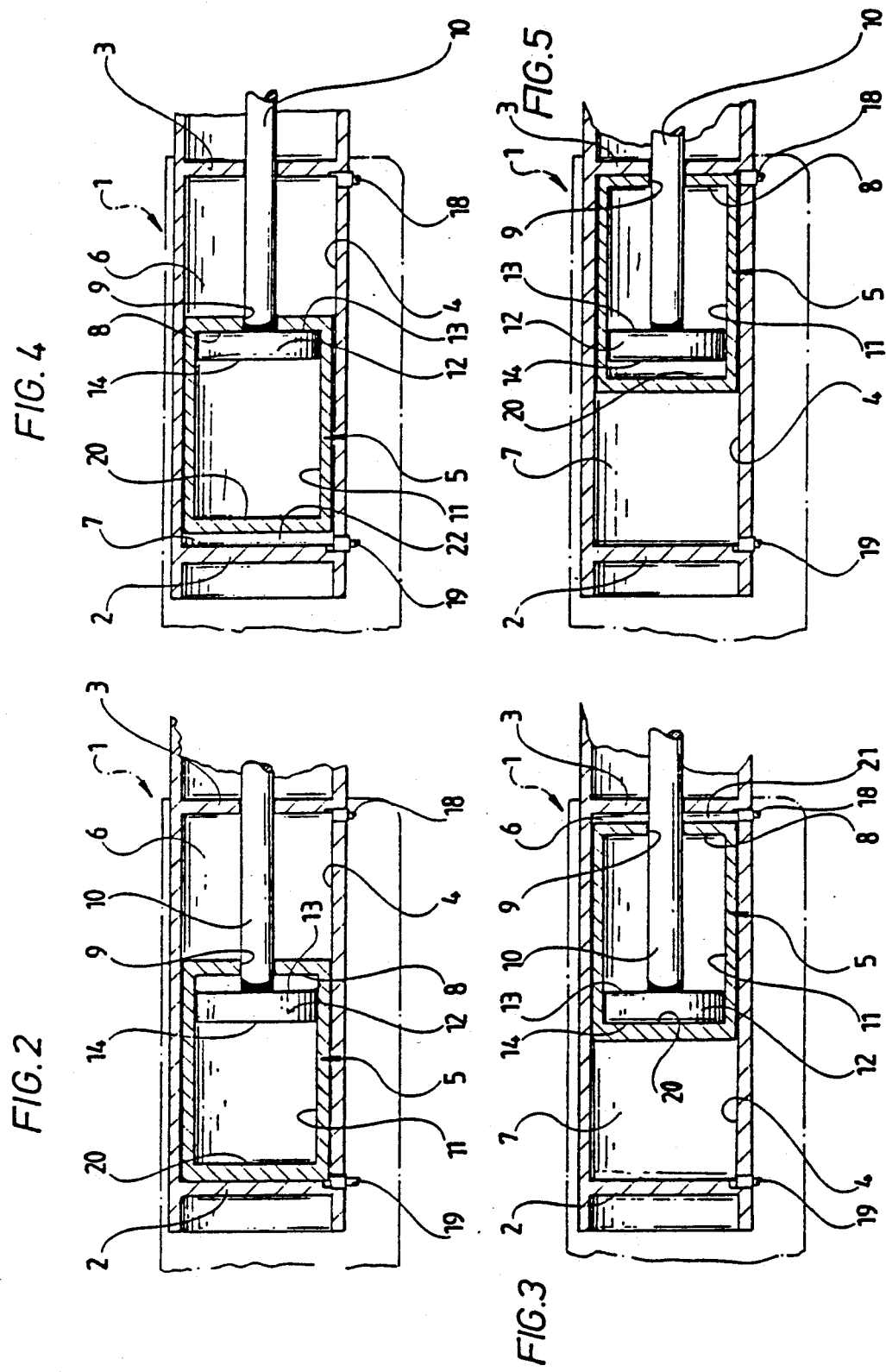

STRIKING TOOL FOR SURGICAL INSTRUMENTS

The invention relates to a striking tool for surgical instruments with a sleeve-shaped gripping part, a tool holder which is slidingly displaceable in the latter in the longitudinal direction thereof, and an oscillatingly driven piston which is slidingly displaceable in the gripping part in the longitudinal direction thereof and has two striking surfaces which strike corresponding contact surfaces of the tool holder and thereby act upon the latter with impulses acting in opposite directions.

Striking tools are used in surgery, for example, to drive rasps into the marrow cavity of a bone and to thus prepare this marrow cavity for receiving an endoprosthesis, or to insert prosthesis shafts into the marrow cavity of bones. In this connection, it is known to use as striking tools, for example, tools which have an oscillatingly driven striking piston which with each stroke of its motion strikes against a tool holder and hence delivers a blow to the tool holder to drive the tool into the bone. This piston can be oscillatingly driven, for example, pneumatically by valves being correspondingly reversed.

It is, furthermore, known to so design such an instrument that with each stroke of the striking piston, not only a blow acting upon the instrument in the forward direction is delivered to the instrument driven into the bone but also a blow acting in the opposite direction so with each stroke, the instrument is also loosened again relative to the bone cavity (EP-B1 144 005). In the known construction, this is achieved by the piston striking against oppositely arranged stop faces on the tool holder at the end of its motion and by the instrument being axially immovably connected to the tool holder. With each stroke, blows acting in opposite directions are thereby transmitted to the instrument.

Such an instrument is suitable for driving in rasps, prosthesis shafts, etc., but not for pulling out such instruments, for example, for pulling out a rasp which is firmly seated in the marrow cavity of a bone.

On the other hand, striking hammers which operate with a flying piston are used in various technical fields. In a known pneumatic chisel for automobile bodies, one compressed air channel each is connected to the front and to the rear cylinder chamber. The compressed air channels are alternately connected to a source of compressed air via a flutter valve. Arranged in the front region of the rear cylinder chamber is an air-release bore which during forward drive is initially closed by the flying piston and is opened shortly before the axially displaceably mounted chisel is struck, the pressure head forming in front of the piston escaping through a clearance between the chisel pin and the guide bore in the housing. Once the air-release bore is exposed, the flutter valve changes over as a result of the drop in pressure so the front cylinder chamber is now subjected to compressed air and drives the piston rearwardly, i.e., away from the tool. When the air-release valve is then closed again by the piston, there is a build-up of pressure again in the rear cylinder chamber which finally reverses the two-way acting valve and initiates the next forward stroke. In this construction, the flying piston does not strike the cylinder housing. The device is, however, unsuitable for medical purposes, above all, because the tool is acted upon only in the direction towards the object, i.e., a rasp could not be pulled out.

There is, furthermore, known from DE 32 29 309 C 2 a hydraulic striking hammer provided with a flying hollow piston which has a striking pin designed as a piston and acting upon a tool axially displaceably mounted therein. By means of a certain guidance of the hydraulic medium and a two-way acting valve, the hollow piston and the piston-type striking pin are alternately driven against an intermediate piston abutting on the tool. This device operates only when the tool is pressed against the object. Here, too, use for the performance of operations in the medical field is excluded.

Bone surgery also includes driving in and out marrow nails, compacting bone tissue and bone cement and working on bones with a chisel. To date, these measures are likewise carried out solely by hand with the aid of a hammer.

The object of the invention is to so improve a generic striking tool that the operator can selectively use it to drive in and pull out an instrument without any conversion work.

This object is accomplished, in accordance with the invention, in a striking tool of the kind described at the beginning in that the actual stroke of the piston is limited by stops in the gripping part such that it is smaller than the double-strike-stroke which the piston would have to cover, with the tool holder held firmly in the gripping part, from the striking of the first striking surface against the first contact surface to the striking of the second striking surface against the second contact surface, and in that the tool holder is mounted for sliding displacement in the gripping part both relative to the gripping part and relative to the piston.

Such a striking tool delivers only forwardly directed blows to the instrument held in it when the operator presses the gripping part in the driving-in direction against the bone. On the other hand, it delivers blows to the instrument which drive the instrument out of the bone when the operator pulls the gripping part away from the bone. This results from the fact that due to the delimitation of the piston stroke, during one stroke of the piston always only either the one or the other striking surface of the piston can strike against the corresponding contact surface of the tool, but it is impossible for both striking surfaces to strike against the respective other contact surface during one stroke. Whichever of the two striking surfaces strikes against its contact surface is determined by the position of the contact surfaces of the tool within the stroke of the piston. This stroke of the piston which is defined by the design of the gripping part is displaceable relative to the tool by the gripping part being displaced relative to the bone in which the tool is held. Simply by pressing or pushing the gripping part, the operator can, therefore, reverse the direction of the striking effect, and the actual movement of the gripping part during the changeover of the direction of the force can be minimal. It may, for example, suffice for the gripping part to be displaced 1 mm relative to the tool to obtain a reversal of the striking direction.

This possibility of reversing the striking direction also gives the operator the opportunity, during insertion of a prosthesis shaft, of briefly loosening the prosthesis somewhat again after it has been partially driven in, in order to check the seating or correct the driving-in direction. This requires no adjustments whatever to the tool itself and so such a reversal can be carried out with an extremely high degree of sensitivity.

In a preferred embodiment, provision is made for the piston to comprise an interior which the tool holder enters through an end face of the piston, for the contact surfaces of the tool holder pointing in opposite directions to be arranged in the interior of the piston, and for the striking surfaces of the piston to also be located in this interior. This results in a particularly space-saving configuration.

Herein, it is advantageous for the tool holder to carry at its end arranged inside the piston an annular flange, the opposite end faces of which form the two contact surfaces.

Furthermore, the end faces delimiting the interior of the piston can form the two striking surfaces.

It may suffice for the stroke of the piston to be only approximately 1 mm smaller than the double-strike stroke, i.e., the stroke during which both striking surfaces would strike against the corresponding contact surfaces. This results in a low structural height of the instrument and also in a very sensitive reversal of the direction of the striking effect.

The air-release bore of the rear cylinder chamber is closed during the rearward motion of the piston so a pressure cushion builds up in the cylinder chamber to damp the rearward motion of the piston and, therefore, the piston does not strike hard against the rear wall of the cylinder chamber. Similarly, an air cushion which absorbs the motion of the piston builds up in the front intermediate chamber, as the ventilation bores have a narrow cross-section. Hence, in the preferred embodiment, the reversing motion of the piston is damped and so the operator has a tool at his disposal which is not subjected to hard blows and, therefore, lies relatively steadily in his hand.

The kinetic energy of the hollow piston extends approximately sinusoidally over the length of the stroke, the maximum being above the air-release bore. By the pressing of the device against the object to be treated, the striking energy can be controlled by the head of the striking pin being displaced over the—in the striking direction—front, decreasing energy zone to the maximum and beyond that into the rear increasing energy zone. To pull a marrow nail or the like out of its seating, the tool is connected to the object to be pulled out. By pulling the device away, the head of the striking pin comes into the stroke of the front end wall of the hollow piston which during its rearward motion strikes against the head of the striking pin and hence performs pulling work. The rearwardly directed striking energy can also be controlled by the surgeon exerting stronger or less strong "pulling-away forces". A further advantage is that practically no striking energy is transmitted to the housing. The device can, therefore, be guided without difficulty and, above all, also permits exact positioning of the tool.

In order that the pneumatic striking tool may be selectively equipped with various tools, the tool is expediently releasably connected to the striking pin by a bayonet-joint or the like.

In order to change the maximum striking energy, there is also the possibility of designing the air-release bore such that it can be offset parallel to the longitudinal axis of the cylinder, for example, by a slider provided with the air-release channel.

In a modified construction of a striking tool, provision may be made for the tool to be positively connected to the striking pin in the pulling and pressing directions and for the striking pin to be provided with a head piece which is guided into the stroke of the front or rear end wall of the hollow piston by axial displacement of the tool, the length of the cavity in the hollow piston being smaller than the length of the stroke. In this construction, the piston strikes against the striking pin during both the forward and the rearward motion so the tool is struck in both directions. When working with rasps, for example, this may prove advantageous for preventing the rasping tool from becoming lodged. In this special construction, the head of the striking cylinder lies both in the stroke of the rearward end wall and in the stroke of the front end wall.

Figure 6:
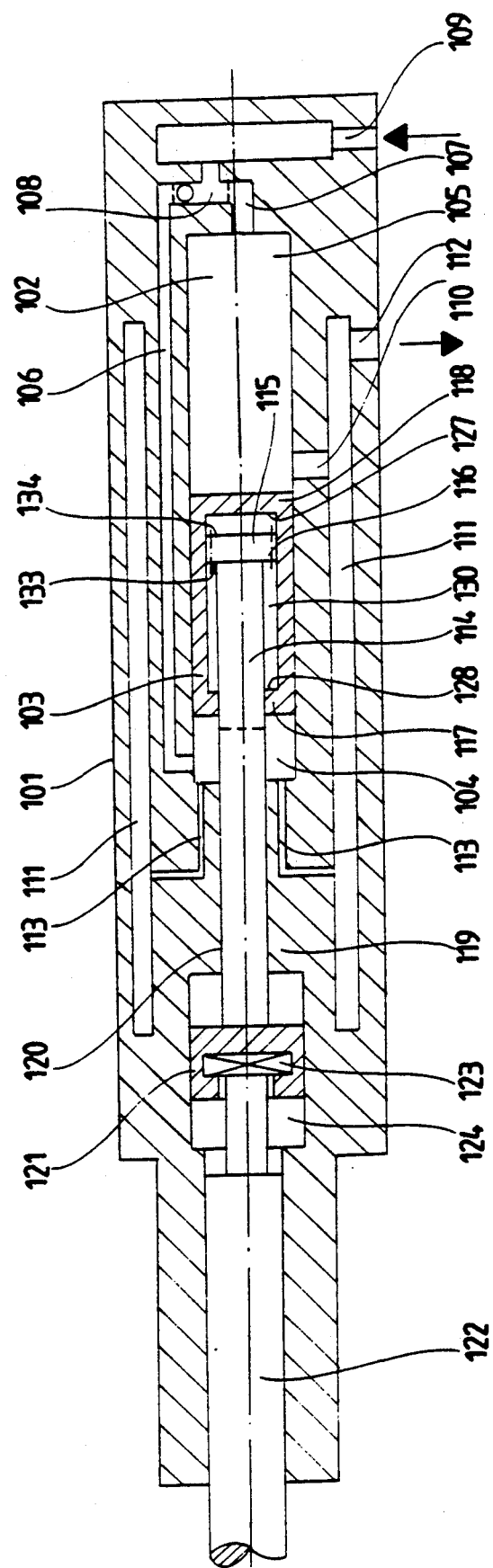

The following description of preferred embodiments serves in conjunction with the drawings to explain the invention in further detail. The drawings show:

FIG. 1 a longitudinal sectional view of a rasp-shaped striking tool in the initial position;

FIG. 2 a schematic illustration of the piston position and the tool position while the tool is striking and with the piston retracted;

FIG. 3 a view similar to FIG. 2 while the tool is striking with the piston in the striking position;

FIG. 4 a view similar to FIG. 2 while the tool is being pulled out with the piston in the pulling-out position;

FIG. 5 a view similar to FIG. 4 while the tool is being pulled out with the piston pushed forward; and FIG. 6 a longitudinal sectional view of a modified embodiment of a surgical striking tool.

The striking tool illustrated in FIGS. 1 to 5 comprises a sleeve-shaped gripping part 1 with a cylinder space 4 closed on both sides by walls 2 and 3. A piston 5 mounted in a sealed and slidingly displaceable manner in the cylinder space 4 divides it into a front chamber 6 and a rear chamber 7. The piston 5 is of hollow configuration and comprises in its front end wall 8 a central opening 9 through which a rod 10 extends into the interior 11 of the piston 5. This rod 10 carries at its free end arranged in the interior 11 an annular flange 12 whose surface facing the rod 10 forms a front stop face 13 while the opposite end surface of the annular flange 12 forms a rear stop face 14.

The rod 10 also extends in a sealed manner through the front wall 3 of the cylinder space 4 and is integrally connected there to a tool holder 15 which is mounted for longitudinal displacement in the gripping part 1. Inserted into the tool holder 15 in a manner not illustrated in further detail is an instrument, for example, a rasp 16 which tapers towards the front end and is used to widen the marrow cavity of a bone 17. The tool is held in an axially immovable manner in the tool holder 15 and can be guided by further guide means, not illustrated in further detail in the drawings, in the longitudinal direction in the gripping part.

A pressure medium pipe 18 and 19, respectively, opens into the front chamber 6 and into the rear chamber 7, respectively. The pressure medium pipes are alternately connected to a source of compressed air by a control means arranged in the rear region, not illustrated in the drawings, of the gripping part 1, while additional air-release valves may be provided to ventilate that chamber of the cylinder space 4 which is not connected to the source of pressure medium. These air-release valves are not illustrated in the drawings. Such pneumatic drivers for the periodically oscillating movement of a piston in a cylinder space are known per se and will, therefore, not be explained in detail herein.

The periodic stroke movement of the piston 5 in the cylinder space 4 is limited by the walls 2 and 3 acting as stop and so a maximum stroke of the piston 5 in the cylinder space 4 is equal to the difference between the spacing of the two walls 2 and 3 and the axial length of the piston 5. In FIG. 1, the maximum stroke of the piston 5 in the cylinder space 4 is designated $H_1$.

The piston 5 is freely displaceable relative to the rod 10 extending into its interior 11. The distance of this relative displacement is determined by the position of the stop faces 13 and 14 as well as the position of the front end wall 8 delimiting the interior and of the opposite rear end wall 20 of the interior 11. The stroke of this relative displacement is designated $H_2$ in FIG. 1. $H_2$ designates the stroke which the rod 10 with the annular flange 12 would have to execute relative to the piston 5 in order for the annular flange 12 to strike both the front end wall 8 and the rear end wall 20. This stroke is referred to hereinafter as double-strike stroke for when the piston 5 executes a stroke which is as large as or larger than this double-strike stroke, the piston then strikes the annular flange 12 in both directions of movement and hence delivers during each movement period both a forwardly directed and a rearwardly directed blow to the annular flange 12 and the tool holder connected to it.

In accordance with the invention, however, the stroke of the piston 5 is so dimensioned that it is smaller than the double-strike stroke $H_2$. Consequently, during a period of the piston movement, the piston can only strike either the front or the rear stop face 13 or 14, respectively, of the annular flange 12, i.e., during each period of the piston stroke only either a forwardly or a rearwardly directed blow is exerted on the tool holder 15.

From FIGS. 2 to 5 it is apparent how the operator may select the direction in which blows are transmitted.

In the embodiment of FIG. 1, the striking tool is shown in its initial position in which striking is not yet possible. In order to bring the striking tool into the working position, pressure medium, for example, compressed air is first introduced into the rear chamber 7 via the rear pressure medium pipe 19. The piston 5 is thereby displaced forwardly and takes the tool holder 15 forward with it until the control means of the drive reverses the direction of the piston until the piston strikes the rear wall 2 again, as illustrated in FIG. 2. The annular flange 12 is not taken along into the retracted initial position illustrated in FIG. 1 but remains—as shown in FIG. 2—in the pushed-forward position.

When the piston is driven in the forward direction again by the control means, its rear end wall 20, therefore, hits the rear stop face 14 of the annular flange 12 and hence exerts a blow on it which drives the tool into a bone, as illustrated in FIG. 3. The stop on the annular flange 12 prevents the piston 5 from reaching the front wall 3 of the cylinder space 4, i.e., a slight gap 21 remains between the piston 5 and the front wall 3. Thus, with this mode of operation, the forward movement of the piston 5 is limited by the annular flange 12 only. The width of the gap 21 may differ and depends only on how far the annular flange 12 is pushed into the interior of the gripping part 1. This pushing-in can be varied by the operator by pushing the gripping part 1 more or less against the bone as the gripping part is freely displaceable relative to the tool. It is thereby also possible for the operator to influence the size of the piston stroke, because with a large gap 21, the piston covers only a small stroke and its movement can, therefore, not be accelerated as strongly as in the case of a large stroke.

By pushing the gripping part forward with sensitivity relative to the bone, the operator thus has the possibility of varying the force of the blow to a certain extent.

Conversely, when the operator pulls the gripping part 1 away from the bone 17, the annular flange 12 is displaced in the direction towards the front wall 3 of the cylinder space 4, since the tool is held firmly in the bone. Consequently, during the rearward movement, the piston 5 strikes the annular flange 12 with its front end wall 8 before the piston can strike the rear wall 2 of the cylinder space 4, i.e., there now remains a gap 22 (FIG. 4) between piston 5 and rear wall 2 of cylinder space 4.

During the forward movement of the piston, in this position of the annular flange, the piston strikes the front wall 3 of the cylinder space 4, with the annular flange 12 not being hit (FIG. 5), i.e., during the forward movement, a blow is not delivered to the annular flange and hence to the tool holder. Thus, by pulling the gripping part away from the bone, the operator causes blows to be delivered to the tool holder in the pulling-out direction only. Here, too, the operator can control the distance covered by the piston from the front end position (FIG. 5) to the stop position (FIG. 4) on the annular flange, i.e., the distance of acceleration it covers, by changing the position of the gripping part 1 relative to the tool holder.

In the embodiments described so far, the gripping part 1 is optionally displaceable relative to the tool holder and so the operator can freely select the position of the annular flange 12 along the cylinder space 4. Embodiments are also possible wherein the displaceability of the tool holder relative to the gripping part 1 is limited so the displacement is only just enough to bring about a reversal of the striking direction, while a variation in the free distance of acceleration of the piston until it strikes the annular flange is only possible to a slight degree.

The further embodiment of a pneumatic striking tool shown in FIG. 6 comprises a cylinder housing 101 with a cylinder chamber 102. In the cylinder chamber 102 there is a flying hollow piston 103 which divides the cylinder chamber 102 into a front cylinder chamber 104 and a rearward or rear cylinder chamber 105. The hollow piston 103 is somewhat shorter than half of the length of the cylinder chamber 102. A compressed air channel 106 and 107, respectively, opens into the front and rear cylinder chamber 104 and 105, respectively. Both compressed air channels 106, 107 are alternately connected to a source of compressed air via a two-way acting valve 108 and a connecting bore. The cylinder chamber 102 is furthermore provided with an air release-bore 110 which opens into an annular air-release chamber 111. An air-release channel 112 adjoins the air-release chamber 111. The air-release bore 110 is arranged in the front section of the rearward or rear half of the cylinder chamber 105, i.e., it is located at a point somewhat behind the half-way point of the length of the chamber. Finally, air-release channels 113 likewise opening into the air-release chamber 111 are associated with the front cylinder chamber 104. These air-release channels 113 serve to release in a damping manner the pressure head built up in front of the hollow piston 103 and, therefore, have a small diameter.

The cylinder housing 101 is provided with a striking pin 114 which is mounted for axial displacement and extends with a head piece 115 into the cylindrical cavity 130 of the hollow piston 103. The piston-like head piece 115 is provided with balance boreholes 116 which serve to balance the pressure. It forms a stop element with stop faces 133 and 134, respectively, which is acted upon by the ring-shaped inside surface 128 of the front end wall 117 and by the circular inside surface 127 of the rear end wall 118 of the hollow piston 103. The striking pin 114 is guided for axial displacement and secured against rotation in the central region by an axial hexagonal bore 120 in an intermediate wall 119. A coupling claw 121 for attachment of a tool 122 is arranged at the front end of the striking pin 114. The releasable attachment is of such design that upon axial displacement of the tool 122, the striking pin 114 is taken along in a corresponding manner. For such a rigid coupling, the tool 122 is provided with a hammer-like coupling head 123 which is insertable in the fashion of a bayonet-joint into the coupling claw 121 of the striking pin 114. The coupling claw 121 is located in a guide chamber 124 which limits the axial displacement of the striking pin 114.

The striking tool operates as follows: After connection to a source of compressed air, the flying hollow piston 103 is reciprocated in the cylinder chamber 102, with the compressed air acting alternately on the front and rear cylinder chambers 104, 105 via the two-way acting valve 108. During the forward drive, the air-release bore 110 is initially closed by the hollow piston 103. Once the hollow piston 103 has been driven forward to the extent that the air-release bore 110 is exposed, the pressure in the rear cylinder chamber 105 is abruptly reduced and the two-way acting valve 108 which may, for example, be a flutter valve is reversed. During the forward drive of the hollow piston 103, the pressure head formed in the front cylinder chamber 104 is slowly reduced with a damping effect via the air-release channels 113. After reversal of the two-way acting valve 108, the hollow piston 103 moves towards the rear and closes the air-release bore 110. In the rear cylinder chamber 105, a pressure is now built up which finally reverses the two-way acting valve 108 again. The air-release channels 113 have such a small cross-section that in the course of the rearward stroke during which the pressure of the pressure source acts upon the front cylinder chamber 104, no considerable pressure drop occurs.

So long as no pressing or pulling force is acting on the striking pin 114, the head piece 115 remains in a central position in which it is not acted upon by the flying hollow piston 103.

If, however, a rearwardly directed force is exerted on the tool 122 which displaces the striking pin 114 rearwards, the head piece 115 comes into the stroke of the rear end wall 118 of the hollow piston 103 and so this end wall 118 strikes the head piece 115 during each forward stroke. By displacement of the striking pin 114, i.e., by the tool 122 pressing on the object to be treated, the striking energy to be transmitted can be altered. The hollow piston 103 possesses the highest kinetic energy at the moment when it exposes the air-release bore 110 during the forward stroke.

If, however, a forwardly pulling force is exerted on the tool 122 which displaces the striking pin 114 forwards, the head piece 115 comes into the stroke of the front end wall 117 of the hollow piston 103 and so this end wall 117 strikes the head piece 115 during each rearward stroke. This rearwardly directed striking energy can be used to pull objects, for example, to pull out bone nails. During this pulling operation, too, the striking energy to be transmitted is controllable by displacement of the striking pin 114, i.e., by a pulling force which is to be brought about by the operator.

We claim:

1. A striking tool for surgical instruments, having a sleeve-shaped gripping part, a tool holder which is slidingly displaceable in the latter in the longitudinal direction thereof, and an oscillatingly driven piston which is slidingly displaceable in said gripping part in the longitudinal direction thereof and which has first and second striking surfaces which strike corresponding first and second contact surfaces, respectively, of said tool holder and thereby act upon the latter with impulses acting in opposite directions, comprising means within said gripping part for limiting the actual stroke of said piston in said gripping part is limited to a distance that is smaller than that required for the piston to travel from a mutual contact of said first striking and contact surfaces to a mutual contact of said second striking and contact surfaces, and means for mounting said tool holder for sliding displacement in said gripping part both relative to said gripping part and relative to said piston, wherein the direction in which said tool holder is driven depends on the relative longitudinal position of said gripping part with respect to said tool holder.

2. Striking tool according to claim 1, characterized in that said piston comprises an interior which said tool holder enters through an end face of said piston, in that said contact surfaces of said tool holder which point in opposite directions are arranged in said interior of said piston, and in that said striking surfaces of said piston are also located in this interior.

3. Striking tool according to claim 2, characterized in that said tool holder carries at its end arranged inside said piston an annular flange, the opposite end faces of which form said first and second contact surfaces.

4. Striking tool according to claim 3, characterized in that said end faces delimiting said interior of said piston form said first and second striking surfaces.

5. Striking tool according to claim 1, characterized in that said stroke of said piston is about only 1 mm smaller than that required for the piston to travel from a mutual contact of said first striking and contact surfaces to a mutual contact of said second striking and contact surfaces.

6. Striking tool according to claim 1, characterized in that the length of the stroke of said tool holder is delimited by stop elements.

7. Striking tool according to claim 1, characterized in that a tool is releasably connected to said tool holder by a closure means.

8. A striking tool for surgical instruments consisting of a cylinder housing, a flying hollow piston in which a striking pin acting upon a tool is mounted for axial displacement, compressed air channels opening into the front and rear cylinder chambers, respectively, and alternatively connectable to a source of compressed air via a two-way acting valve, and an air-release bore, characterized in that said tool is positively connected to said striking pin in the pulling and pressing directions, and said striking pin is provided with a head piece which is guided into the stroke of said front and rear end walls of said hollow piston by axial displacement of said tool, the length of said cavity in said hollow piston being smaller than the length of the stroke thereof.

9. Striking tool according to claim 8, characterized in that said hollow piston is shorter than half of the length of a cylinder chamber provided in said cylinder housing to carry said piston, and an air-release bore is arranged in a front section of a rear half of said cylinder chamber.

10. Striking tool according to claim 9, characterized in that air-release bores with a minimal cross-sectional area are arranged in a front half of said cylinder chamber.

11. Striking tool according to claim 10, characterized in that said air-release bore is designed such that it can be offset parallel to the longitudinal axis of said cylinder.

12. Striking tool according to claim 9, characterized in that said air-release bore is designed such that it can be offset parallel to the longitudinal axis of said cylinder.

* * * * *

UNITED STATES PATENT AND TRADEMARK OFFICE
CERTIFICATE OF CORRECTION

PATENT NO. : 5,108,400

DATED : April 28, 1992

INVENTOR(S) : Appel, et al.

It is certified that error appears in the above-identified patent and that said Letters Patent is hereby corrected as shown below:

In claim 1, at column 8, line 16, delete "is limited".

Signed and Sealed this

Third Day of August, 1993

Attest:

MICHAEL K. KIRK

*Attesting Officer*   *Acting Commissioner of Patents and Trademarks*